(12) United States Patent
Paulson

(10) Patent No.: US 8,601,875 B2
(45) Date of Patent: Dec. 10, 2013

(54) DEVICE AND METHOD TO ASSESS IMPAIRMENT OF PIPELINE WALL STRENGTH

(75) Inventor: Peter O. Paulson, Calgary (CA)

(73) Assignee: Pure Technologies Ltd., Calgary, Alberta (CA)

( * ) Notice: Subject to any disclaimer, the term of this patent is extended or adjusted under 35 U.S.C. 154(b) by 326 days.

(21) Appl. No.: 13/057,211

(22) PCT Filed: Aug. 5, 2009

(86) PCT No.: PCT/CA2009/001099
§ 371 (c)(1),
(2), (4) Date: Mar. 24, 2011

(87) PCT Pub. No.: WO2010/015082
PCT Pub. Date: Feb. 11, 2010

(65) Prior Publication Data
US 2011/0162454 A1    Jul. 7, 2011

Related U.S. Application Data

(60) Provisional application No. 61/086,212, filed on Aug. 5, 2008, provisional application No. 61/161,148, filed on Mar. 18, 2009.

(51) Int. Cl.
*G01N 29/07* (2006.01)

(52) U.S. Cl.
USPC ............................................. 73/598; 73/623

(58) Field of Classification Search
USPC ..................... 73/592, 597, 598, 623
See application file for complete search history.

(56) References Cited

U.S. PATENT DOCUMENTS

| | | | | | |
|---|---|---|---|---|---|
| 5,970,434 | A | * | 10/1999 | Brophy et al. | 702/170 |
| 7,104,125 | B2 | * | 9/2006 | Harthorn et al. | 73/152.57 |
| 2006/0283251 | A1 | * | 12/2006 | Hunaidi et al. | 73/597 |

\* cited by examiner

*Primary Examiner* — John Chapman, Jr.
(74) *Attorney, Agent, or Firm* — Ridout & Maybee LLP; Daphne L. Maravei

(57) ABSTRACT

The invention locates impaired sections of a pipeline, such as sections where the wall of the pipeline has been weakened or thinned. It provides a moveable device which passes through the pipeline and which has a first station. The moveable device has means to locate its position accurately. There is a second station, which is mounted either on the moveable device or in association with a fixed location on the pipeline wall. Either the first station or the second station has an acoustic or seismic pulse generator, and the other has a pulse receiver. The time taken for a pulse to travel from the pulse generator to the receiver is found to vary with the condition of the pipeline wall at the location where the moveable device is located at the time it receives (or sends) the pulse. The rate of change of velocity of the pulse as the device passes different locations in the pipeline is also found to vary with the condition of the pipeline wall at such location.

17 Claims, 5 Drawing Sheets

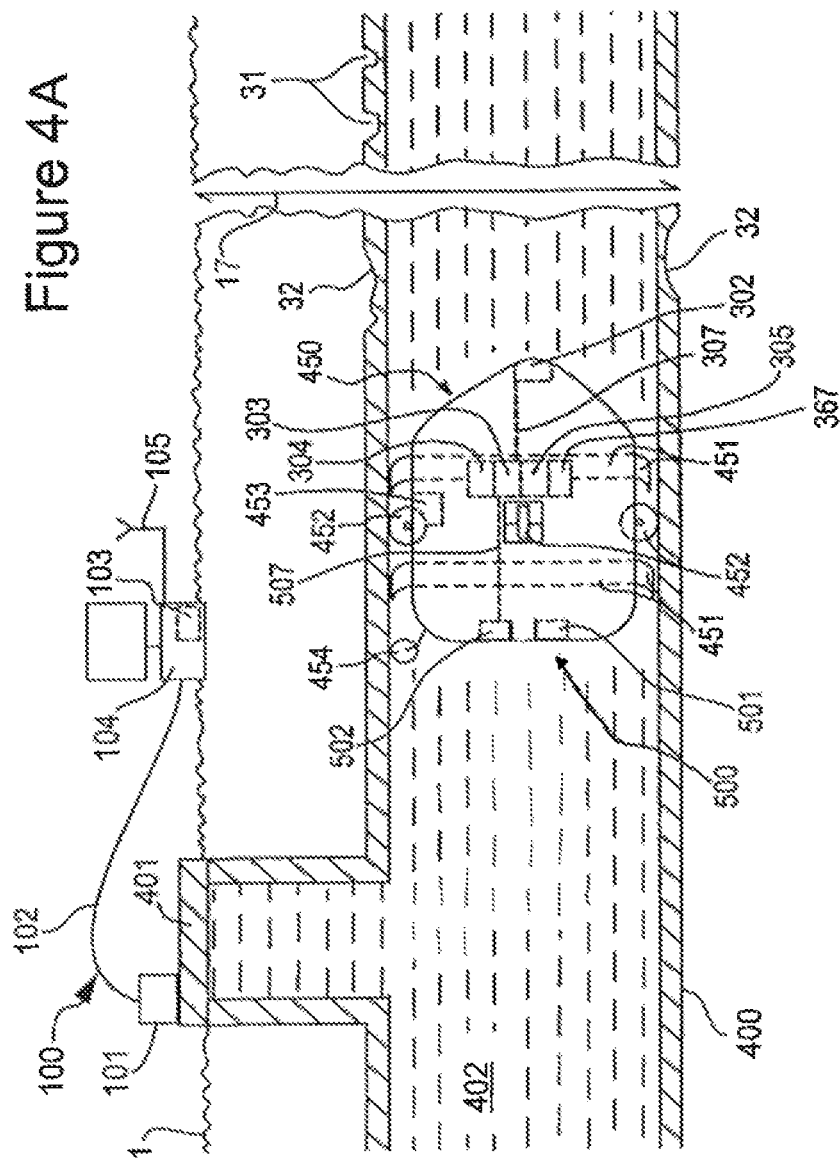

DEVICE AND METHOD TO ASSESS IMPAIRMENT OF PIPELINE WALL STRENGTH

This application claims the benefit of U.S. Provisional Application No. 61/086,212, filed Aug. 5, 2008, and U.S. Provisional Application No. 61/161,148, filed Mar. 18, 2009.

FIELD OF THE INVENTION

This invention relates to a device and method to locate impairments in pipeline wall strength. Such impairments can occur because of wall thinning or degradation or damage to the wall material.

BACKGROUND

Pipelines are made of many different materials, including ductile iron, cast iron, welded steel, plastic, asbestos cement and concrete. They carry many different materials, such as water, waste, oil, gas, or chemical products. Many pipelines are buried underground, and are exposed to exterior corrosion and abrasion from the earth, gravel, sand or like material in which they are buried or from corrosive or abrasive substances within such material. Other pipelines suffer corrosion because of electrical charges, or become abraded and/or corroded by the material carried in the pipeline. Corrosion can cause pitting in metal pipelines, and breaking of reinforcing wires in concrete pipelines which have wire reinforcements within their walls. Pipelines can also be damaged or weakened by action caused by humans, as for example by heavy equipment passing over a buried pipeline.

In use, therefore, the walls of pipelines tend to become thinner and/or weaker over time. This can lead to rupture of the pipeline. It is therefore useful to determine those parts of the pipeline which are suffering from weakness or which have thinned, so that corrective action can be taken before the pipeline ruptures in a thinned or weakened location.

Current commercial methods of assessing wall thickness and/or strength are not very practical or cost-effective. It is possible to excavate a portion of a pipeline and make a small hole to get a sample (called a "coupon") of the pipeline wall. This permits a direct measurement of the wall thickness and condition where the sample is taken. However, things which could cause thinning or weakening of a pipeline wall do not necessarily occur uniformly along the length of the pipeline. Therefore, a coupon reveals the situation at the precise location where it is taken, but does not necessarily give useful information about other locations along the pipeline.

It is also known to take direct ultrasonic measurements of pipeline wall thickness where a pipeline is exposed (i.e. not buried in the ground or otherwise inaccessible.) This is cheaper than taking coupons, but it is limited to exposed locations, and does not necessarily give useful information about other locations along the pipeline.

Acoustic measurement has also been used, as described for example in Hunaidi U.S. Pat. No. 6,591,032 and Hunaidi et al U.S. Pat. No. 7,328,618. By this method, the propagation velocity of a low frequency disturbance such as a release of fluid from a pressurized pipe or ambient pipe noise is determined by measuring the times at which the wave caused by this disturbance passes two fixed points which are spaced from each other by a known distance, for example two hydrants in a water line. The propagation velocity so determined is compared with a theoretically calculated velocity. The result is a figure which is said to represent the average thinning of the pipeline walls over the fixed distance. The average figure does not determine any specific locations between the fixed points where extreme thinning has occurred, or even reveal whether locations having greater-than-average thinning exist.

In some pipelines (particularly in the oil and gas industry), pipeline pigs are used to perform cleaning and data-gathering functions. Such pigs can be fitted with devices, such as ultrasonic measuring devices or magnetic flux measuring devices, which can determine wall thickness. However, the practical use of an instrumented pipeline pig is limited to pipelines which have pigging stations and which do not have sharp bends.

In some very large diameter pipelines, it has been possible to drain the pipeline and have personnel equipped with ultrasonic or similar devices take direct measurements at selected locations by walking through the pipeline to these locations. The draining of the pipeline takes it out of service, so this method is not suited to frequent checking of wall thickness.

It would be very useful to be able to determine where along the length of a pipeline the walls had become impaired, either by becoming thinner and/or weaker. It would be even more useful to be able to measure a quantitative value which represents relative impairment at locations along the pipeline. This information would permit appropriate maintenance or replacement to be undertaken of only those pipeline sections where the thinning or weakening had progressed to an undue extent.

SUMMARY OF THE INVENTION

According to the invention, a moveable inspection device passes through a pipeline which contains a gas or liquid, preferably a liquid, such as for example oil or water. The device is equipped so that its location or its distance of travel though the pipeline is known or can be calculated easily.

The device has a first station, and is used in association with a second station. The second station can be on the device, but spaced from the first station, or can be at or associated with a fixed location on the pipeline wall, or in a less preferred embodiment, can be on another moveable device which has a known location in the pipeline. One of the first and second stations is equipped with an acoustic or seismic pulse generator (hereinafter called the "pulse generator") which generates pulses of low-frequency acoustic or seismic waves, and the other is equipped with a receiver for such waves. The waves have wavelengths larger than the diameter of the pipe. The receiver is associated with data storage to store the received signal or with computer means to analyze the signal instantaneously.

In a first embodiment, the second station is on the moveable device, so that both the pulse generator and the receiver are on the moveable device, but are spaced a known distance from one another.

In a second embodiment, the second station is at a fixed location on the pipeline. It need not be on the pipeline wall itself, but can be on a structure associated with the pipeline such as a hydrant, hatch cover or like structure which transmits seismic or acoustic waves to a fixed location on the pipeline wall.

In a third, non-preferred embodiment, the second station is on another moveable device, the location of which in the pipeline is known or can be calculated.

The pulse generator sends out pulses at known times or intervals. The receiver has a means for time measurement associated with it, so that the time of receipt of particular pulses can be determined. Pulses are sent and recorded as the device moves though the pipeline. The presence of thinning and for weakening of the pipeline is found to correlate with variation of the apparent velocity of the pulses measured when the device is at a particular location from the average velocity of the pulses as measured over a longer length of the pipeline. It is also found to correlate to the rate of change in the apparent velocity of the pulses measured when the device is passing a location having such thinning and/or weakening.

BRIEF DESCRIPTION OF THE DRAWINGS

The invention will be illustrated by drawings, in which:

FIG. 4A shows a further alternative embodiment of the invention as shown in FIG. 4.

DETAILED DESCRIPTION OF THE INVENTION

Figure 1:
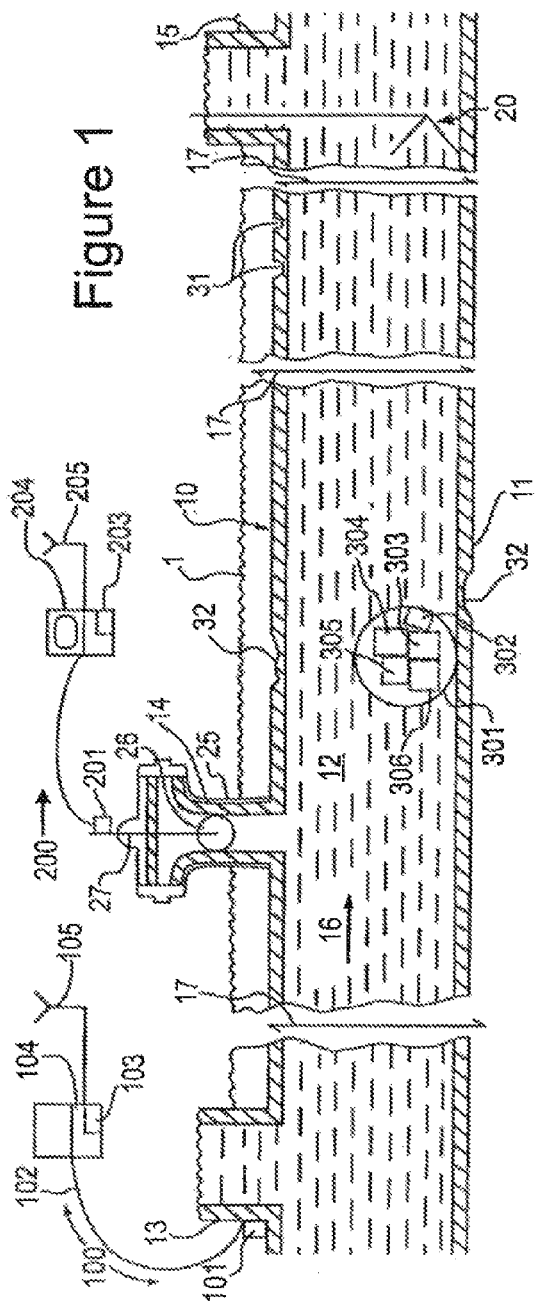
FIG. 1 is a cutaway view, not to scale, of a pipeline in which a ball-like moveable inspection device of the invention rolls along the bottom of the pipeline, propelled by liquid flow.

The invention is useable with pipelines made of ductile iron, cast iron, welded steel, plastic, asbestos cement or concrete, and may also be useable with pipelines of other materials. The pipeline must contain a fluid through which pulses at the frequency or frequencies used can propagate. Preferably, the fluid is a liquid. The particular liquid is not critical, and can be for example water, waste water or sewage, oil, a petroleum product, LNG or a liquid chemical. It is preferred that the pipeline be filled with the liquid and especially preferred that the pipeline pressure be at least slightly higher than atmospheric pressure. However, the invention will work, although usually not as well, when the pipeline is not pressurized and/or when there is an air gap above the liquid, provided that there is a continuous liquid path in the length of pipeline being examined. It will also work in gas-filled pipelines, although the results are not as good as in pipelines containing liquid.

As noted above, the invention requires two stations, at least one of which is on a moveable inspection device. The other can be on the device or at another known or fixed location, on or in the pipeline. Preferably, this location is fixed with respect to the pipeline wall. One of the stations is equipped with a pulse generator to generate pulses of low-frequency acoustic or seismic waves and the other is equipped with a receiver for such waves. Each of the pulse generator and the receiver has a means for determining accurately the time at which it sends or receives (as the case may be) the pulse. In the case of the pulse generator, the means can either be a timing apparatus to generate the low frequency wave pulses at set intervals, or a clock and an associated recording device which records the time at which pulses are sent, or both. In the case of the receiver, the means is a clock and an associated recording device to record the time pulses are received. Where GPS time signals are available, a receiver for such signals preferably is used instead of the clock.

The moveable inspection device also has a means to determine its location in the pipeline.

From the known time that the pulse is generated, and the known time that it is received, the time taken for pulses to travel between the pulse generator and the receiver can be determined. Since the location of the moveable device and its velocity is known or can be determined, the velocity of the waves forming the pulse can be calculated when the receiver is at different locations. Likewise, the rate of change of velocity of the pulses can be determined as the device moves from one location to another.

In the embodiment where the second station is at a fixed location on the pipeline, the pulse generator is preferably located at the second station and the receiver is in the moveable device. This is preferred because there is a greater power requirement to generate pulses than to receive them, and it is easier to supply power in most cases to a fixed location than to a small moving device, except in a case where the moving device is tethered and power can be passed through the tether. For convenience of description, this embodiment of the invention will be described as having the pulse generator on the pipeline and the receiver on the device. It will be evident to one skilled in the art that the invention is also operative when the receiver is on the pipeline and the pulse generator is on the device, provided that the device is supplied with sufficient power to generate the pulses.

The invention is useable in pipelines in which the contained fluid is flowing, or in pipelines where there is no flow. The inspection device is chosen according to the expected flow. If the moveable inspection device is one which intended to be carried along by the flow of the fluid, then there must be sufficient fluid flow to move the device. However, if the device is self-propelled, then there is no need for the fluid in the pipeline to be flowing at the time data is collected according to the invention.

The pipeline also requires means of ingress and egress for the moveable inspection device, so that it can be placed in the pipeline before data collection and removed afterwards. In most pipelines, there are inspection or access ports which are suitable. Additionally, in many water pipelines there are hydrants which can be used, and in many oil pipelines there are pigging stations which can be used.

The moveable inspection device has a means for determining its location along the length of the pipeline. The means chosen depends on the type of inspection device used.

A preferred inspection device is a ball-type untethered inspection device which moves with the flow of liquid in the pipeline as shown in Paulson published application WO2006081671 A1. As disclosed in that application, the location of the inspection device can be determined for example by counting the number of times it has revolved while rolling along the bottom of a pipeline, or by other means as disclosed in that application.

An untethered neutral density ball device as shown in Mecon published application WO2004059274 can also be used as the inspection device. In this type of device, the location is determined by noting when the device passes electromagnetic transmitters which act as beacons at known locations along the pipeline and interpolating points between the beacons to find the speed of travel of the device between the beacons, and hence what its location was at a particular time when it was between the beacons. The same method can also be used for other untethered devices, such as the Paulson one described in published application WO2006081671 A1.

In another embodiment, the device is a tethered inspection device that moves with the flow of the liquid in the pipeline, or is pulled by its tether against the current. In this case, the location of the device can be determined by noting the amount of tether which has been paid out at any time, or by use of an electromagnetic tracking device on the surface of the ground above a buried pipeline as shown in published application WO 0118442 A2 of WRC PLC, or in other known ways.

A device useable in pipelines which have pigging stations is a conventional pipeline pig having conventional means to record the distance that the device has travelled within the pipeline. Such conventional means can be, for example, an odometer or other known device which contacts the wall of the pipeline as the pig moves.

An alternate way of determining the location of the device is by the use of high frequency waves as disclosed in Paulson, PCT application CA2009/000891 filed Jun. 25, 2009. As described in detail in that application, high frequency acoustic emissions are sent from the device and received at a known location, or are sent from the known location and received at the device. The device and the known location are equipped with synchronized time measuring means. For the known location, this can be a link to receive GPS signals or, if the location is not suited to receive GPS signals, a clock. For the device, it is typically a clock, as the device may be used in underground pipelines where GPS signals do not reach. The time of sending of each emission and the time it is received are determined accurately and precisely. The speed of sound of the frequency used in the particular pipeline is known or is determined empirically, and the distance is calculated from the elapsed time and the speed of sound. When this method is used in the present invention with the embodiment having a station at a known fixed location in the pipeline, the known location can conveniently be the station.

In the preferred form of the invention, the inspection device is provided with a time measuring means, the receiver, an associated data recorder, and a power supply. Conveniently the data recorder can utilize a commercially available data storage device, such as a removable SD memory card or flash memory. The power supply can be a compact battery, such as a long-life lithium battery, or (if the device is tethered), a connection to a remote mains power outlet or generator. The data recorder records the time and location of the device or data from which the location can be determined. It also records the time of receipt of low frequency waves as discussed below. The receiver can be a hydrophone which can receive at the frequency used, or an accelerometer. It should be in acoustic or seismic (depending on the receiver) contact with the fluid, so that it can receive pulses passing through the fluid. Suitable hydrophones and accelerometers are available commercially. An example of a suitable hydrophone is model VHLF manufactured by VEMCO Division, AMIRIX Systems Inc., 211 Horseshoe Lake Drive, Halifax, Nova Scotia, Canada B3S 0B9 An example of a suitable commercially available accelerometer is an axially polarized piezo crystal, Model 850 series, available from American Piezo Ceramics division of APC International, Ltd., Duck Run, P.O. Box 180, Mackeyville, Pa. 17750 USA.

In the case of an untethered device, all of the time measuring means, power supply, receiver, data recorder and the receiver are located in the moveable device. The time measuring means is typically a clock, as the device is normally used in locations where GPS signals do not penetrate. However, if the device is intended to travel through a pipeline in which GPS signals can be received reliably, the time measuring means can be a link to receive GPS signals which provide a time readout. In the case of a tethered device, some or all of the time measuring means, power supply and data recorder can be located remotely and connected with the device through its tether.

In operation, the moveable device is permitted to move through the pipeline. In the preferred embodiment, the moveable device is a spherical ball and rolls along the bottom of the pipeline propelled by the flow of fluid in the pipeline in the manner shown in Paulson published application WO2006/081671 A1. The number of revolutions made by the ball as it rolls along the bottom of the pipeline is recorded as in that application, to indicate the distance travelled. If the pipeline is made of wire-wrapped concrete or welded metal, a magnetometer can be present in the ball to record the passing by pipeline joints, to provide a corroboration of the distance travelled.

As it travels along the pipeline, a receiver in the ball receives low frequency pulses generated by a pulse generator at the station. The pulses are recorded for later examination, or could be analyzed by an on-board processor.

If the moveable device is relatively large, such as a robotic crawler vehicle or a pipeline pig, it is possible to mount two spaced receivers on it. These can be spaced, for example 2 meters apart. The distance between them is known precisely. Having two receivers a known distance from one another provides a consistency check on data, and helps reduce some forms of error.

In a first embodiment, used where the mobile device is fairly large, such as a robotic crawler vehicle or a pipeline pig, both the receiver and the second station with the pulse generator are mounted on it, with the distance from the receiver to the pulse generator being known precisely. In this embodiment, the receiver and the pulse generator should be spaced at least about one pipe diameter from one another, and preferably farther if this is possible with the mobile device on which they are placed. For example, in a one-metre diameter pipe, a receiver and a pulse generator spaced exactly 1.5 metre apart on a robotic crawler vehicle provide useful results.

In a second embodiment, the second station is at a fixed location on the pipeline. Conveniently, the pulse generator of the station is temporarily attached to the pipeline at an accessible location, such as an access port, or to an object, such as a hydrant, valve actuator or access port cover which can transmit pulses to the pipeline wall and into the fluid in the pipeline and which is more easily accessible from above ground than is the pipeline wall. Such a structure is called herein a "structure in seismic or acoustic contact with the pipeline". The pulse generator can be connected to its associated data storage and time measuring means either by cables or wirelessly. Conveniently as much of the second station as possible is above-ground, in an area where an operator has easy access. If desired, the operator may also have a computer which monitors the progress of the device, as for example by using the locating apparatus and method described in PCT application CA2009/000891 discussed above.

In an third, non-preferred, embodiment, the second station can be on another device moving through the pipeline, provided that device has means that permit its location to be determined. Use of this embodiment creates additional complexity in calculation, so is not preferred.

Each of the pulse generator and the receiver is in acoustic or seismic contact with the fluid in the pipeline. The pulse generator generates low frequency acoustic or seismic waves. The frequency is such that the wavelength is greater than the diameter of the pipe forming the pipeline so that the waves intersect the pipeline wall and propagate partially through the liquid within the pipeline and partially through the wall of the pipeline back into the liquid from the wall of the pipeline. Suitable pulse generators are available commercially. One such generator is transponder model AA-150-LH of Etrema Products Inc., 2500 North Loop Dr., Ames, Iowa, 50010, USA.

Wavelengths of 1.5-75 times the diameter of the pipeline are useable. The preferred range of wavelengths is from about 5 to about 15 times the diameter of the pipeline. The wavelength generated by a particular frequency depends upon the material of which the pipeline is made, and the fluid inside it, particularly whether the fluid is a gas or liquid. Wavelengths over 15 times the diameter of most commercial pipelines would require very low frequencies, at which noise may become a problem.

Instead of determining the wavelength of sound in a particular pipeline containing a particular fluid, and choosing the wavelength of the pulse to be generated based on this information, it is usually more convenient to select a frequency which is known to give a wavelength which is suitable in pipelines carrying the particular fluid. For example, frequencies of 20 Hz to 2000 Hz have been found to be useful for pipelines of 200 mm to 2000 mm in diameter which carry liquids. However, many liquids absorb frequencies in the range 500 Hz-18000 Hz. If the particular liquid in the pipeline being investigated absorbs such waves, use of frequencies which are absorbed should be avoided.

Having regard to all of these parameters, use of frequencies in the 20 Hz to 500 Hz range is preferred for examination of most commercial pipelines which carry liquids, particularly water, waste water or oil.

As discussed below, it is possible to use a pulse which is a series of sequential shorter pulses (herein called "subpulses") each of predetermined length, immediately after one another. Adjacent subpulses are of different frequencies, with all frequencies being chosen according to the parameters in the previous paragraph.

Once the frequency of the pulse (or the set of frequencies, in the case of a pulse comprised of subpulses) is chosen, it is preferred to install a bandpass filter on the receiver, to exclude all but a narrow band of frequencies above and below that frequency or set of frequencies. This limits the amount of noise received, and makes analysis of results easier. For example, a bandpass filter which excludes frequencies more than 20 Hz above or 20 Hz below the chosen frequency or set of frequencies is suitable. If no bandpass filter is used, it may be advisable to filter out unwanted frequencies prior to analysis of the data stored by the data storage device. A bandpass filter can of course if desired be designed permit entry of another range of very different frequencies, for example a range of high frequencies useable to locate the position of the device using the method of PCT application CA2009/000891.

The pulses are repeated at intervals. The length of the interval between pulses (herein called the "repetition rate") is chosen according to the expected speed of travel of the device though the pipeline, so that there will be pulses received when the moving device is at locations spaced approximately a desired distance from one another. Usually, it is desired to receive a pulse for at least every 0.5-5 m. or so of pipeline traversed, and preferably for every 0.5-1.5 m. of pipeline traversed. At normal pipeline flow speeds, this can be accomplished with one pulse every 1-10 seconds. If desired, pulses can be more frequent, so that the distance travelled by the device between pulses is shorter. If the time between pulses is reduced too much, however, there is a possibility that, when the pulse generator is distant from the receiver, pulses received at the receiver could overlap. This can be avoided by using two different frequencies for alternate pulses. Obviously any bandpass filter arrangement would have to be configured to permit reception of all frequencies being used.

The pulses can be of any convenient length. Generally pulses of about 2-50 milliseconds are preferred, with pulses of 10-30 milliseconds being specially preferred. This provides an interval between pulses which is considerably longer than the pulse length, reducing the possibility of the pulses overlapping if they travel a long distance within the pipeline. A pulse can be of a single frequency, or as noted above it can be made up of subpulses of different frequencies in a predetermined sequence. A reference point is established as the time of receipt of the pulse for calculation purposes. This is the beginning or end of a pulse which is a single frequency. If a pulse is made up of subpluses, reference point can be the beginning or the end of the pulse or a point at which a change of frequency occurs within the pulse. If a pulse made up of several subpulses is used, the pattern of sequential subpulses makes it easier to distinguish the pulse from any ambient noise. Also, if the portion of the pulse containing the reference point is drowned out by noise, it may still be possible to receive enough of the pulse to reconstitute the time at which the reference point would have been received but for the noise.

In most cases, a pulse of a single frequency is suitable and preferred because it is less complicated, but a pulse comprising subpulses may be preferable in a noisy environment.

The waveform for the pulses should be accurate and reproducible. Suitable waveforms can be generated by commercially available sound cards or D/A systems. One suitable commercial product is the Signal Wizard, obtainable from the University of Manchester, U.K.

The distance over which pulses can be received without undue distortion or noise depends on conditions within the pipeline. For example, when the receiver is near a pumping station, noise from the pumping station, tends to drown out the signal. Also, bends in the pipeline tend to attenuate the signal.

In the embodiment where the pulse generator is mounted at a fixed and known location on the pipeline wall and the receiver is on the moveable device, it is useful to have several pulse generators mounted at different known locations. As the moveable device bearing the receiver moves down the pipeline, it will successively pass locations where pulse generators are located. If the signal from one is attenuated by pipeline architecture or distance, the signal from another may be available. Pulse generators, can be placed, for example, at inspection ports or hydrants along the pipeline, and the number of stations can be chosen with regard to pipeline architecture. For example, more stations are preferred in pipelines with frequent bends or sharp bends than in long straight pipelines. Preferably, if there is a sharp bend, there should be pulse generators on straight portions on each side of it. These stations should preferably generate pulses at different frequencies and preferably pulses spaced from each other in time by an interval considerably longer than the pulse length, so that the pulses do not overlap.

The material of which the pipeline is constructed and how the pulse generator is attached also have an effect on the reception of pulses. For example, the pulses can be received reliably over a longer distance in a pipeline made of ductile iron than in a plastic pipeline. Pulses generated by a pulse generator attached directly to the pipeline can be heard at a greater distance than pulses from a pulse generator attached to a hydrant or hydrant actuator or other pipeline accessory in acoustic or seismic contact with the pipeline. Pulses can be detected at longer distances in large pipelines (eg 1-2 m. in diameter) than in pipelines of smaller diameter. The liquid or gas in the pipeline, and whether the pipeline is completely filled with liquid also affect the distance over which the pulses can be detected.

In one preferred embodiment, the receiver is on the moveable inspection device, and there are several stations with pulse generators, placed where the pipeline is easily accessible, as at hydrants or inspection ports. Where possible, it is preferred that these be spaced not more than about 200-300 metres from one another when a ductile iron pipeline is being inspected and not more than about 200 metres from one another when a plastic pipeline is being inspected. In this embodiment, it is preferred that the receiver be in good receiving range of at least two pulse generators at any time during its travel along the pipeline, so that there are at least two results that can be obtained for each location along the pipeline. As the device moves through the pipeline, pulse generator stations that it has passed can be disassembled and reassembled at other accessible locations downstream from the moving device if desired.

As previously noted, in the embodiment where one of the pulse generator and receiver is on the device and the other is mounted in acoustic or seismic contact with the pipeline, each is equipped with a means for measuring time accurately. If the pulse generator or the receiver is in a position to receive GPS signals, its means for measuring time accurately can be a link to the GPS satellite system. The term "GPS signals" in this invention means time signals from the Global Positioning System satellite system. It will be obvious to one skilled in the art that any other highly accurate remotely generated time signal could be used instead of GPS signals, and the time measuring means of the invention is intended to include such signals. If no GPS or comparable system for remote provision of time signals is accessible, a clock is used. Clocks should be chosen for high accuracy and low drift, in order to get accurate data. For example, it is preferred that any clocks used should measure time with an accuracy of at least +/−1 millisecond per hour, with a drift not exceeding 50 microseconds over a period of about 10 pulses. The more accurate and drift-free a clock is, the better, having regard to practical considerations such as cost, size and power consumption. Commercially availabe timing chips can be used, and one skilled in the art will be able to choose a suitable chip.

Generally, the inspection device will not be in GPS communication if it is untethered and passing through a belowground pipeline, so it is provided with a clock. Of course, it could be provided with a GPS receiver instead if the particular pipeline is one in which GSP time signals can reliably be received. A tethered inspection device can use a GPS time signal if the tether connects it to an above ground antenna.

In the embodiment where both the pulse generator and the receiver are mounted on the device, there needs only to be one time measuring means, as the pulse generator and the receiver can share it. Typically, this will be a clock, as the inspection device typically will not be in GPS communication when passing through a buried pipeline.

Usually, all pulse generators or receivers located on the pipeline will be sited where they are in GPS communication, so their time measurement means can all be GPS signals which are automatically synchronized with one another. Pulse generators and receivers on the device will typically share the same clock, so no synchronization is necessary. If one of the pulse generator and the receiver is on the pipeline and the other is on the device, it is preferred (although not absolutely necessary) to synchronize their time measurement means. If both the station on the pipeline and the station on the device use clocks, they are preferably synchronized with one another. If one uses a clock and the other uses a GPS signal, the clock is preferably synchronized to the GPS time signal. However, synchronization need not be done provided that there is little or no clock drift while the pipe inspection is being carried out. If it is done, it can be done either before of after the pipe inspection, and the data from the inspection can be corrected after the inspection to reflect the synchronization.

After the inspection device has passed through the length of pipeline to be examined, it is retrieved and the record of pulses received is examined. For each pulse which is examined, the location of the device at the time at which the reference point for that pulse was received by it is noted or calculated. The time at which the reference point for that pulse was emitted by the pulse generator is also noted.

The time taken for a pulse to travel from the pulse generator to the receiver is found to vary with the condition of the pipeline wall at the location where the moveable device is located at the time it receives (or sends) the pulse.

Several different analyses can then be performed. In one, the travel time of the pulse from its emission by the pulse generator to the location where it is received is then obtained by simple subtraction. This information gives the distance travelled by the pulse and the time taken for it to travel that distance. From this, the velocity of the pulse (distance divided by time) is determined. By doing this calculation for a large number of locations, an average velocity of the pulses can be determined. It is found that, as the device passes through the pipeline the velocity of the sound pulses varies only slightly from the average when the device is at some locations in the pipeline, but that at other locations it is substantially above or below the average, sometimes by as much as 50%. The excursion (movement away from the average) at some locations is in the direction of increased velocity and at others it is in the direction of decreased velocity. It has been found that such variations from the average velocity (whether positive or negative) are indicative of local conditions in the wall of the pipeline in the vicinity of the location where the device was located at the time the pulse was received by the device (if the device has the receiver or has both the receiver and the pulse generator) or sent by the device (if the device has the pulse generator and the receiver is on the pipeline). Local conditions which differ from the average are usually indicative of impairment in the strength or thickness of the pipeline wall. Thus, examination of the records from receipt of a series of pulses gives a record of areas along the pipeline where the wall is probably impaired, for example by thinning or damage. Further, the extent of variation from the average, in terms of percentage from the average) can often give an approximation of how serious the impairment is.

Having regard to the speed of movement of the device in the pipeline, the pulses can be generated at a sufficient spacing to localize the areas of thinning or degradation quite precisely. Indeed, the locations of thinning or degradation have in test situations been found to an accuracy of +/−1 m. along the length of the pipeline. In order to get high accuracy, the signal received at the receiver should be sampled at a high rate, and the data from such sampling stored so that the start (or other chosen reference point) of each pulse can be determined precisely. For example it is preferred to use a sampling rate of 40000 samples per second. Higher sampling rates, for example 96000 samples per second, can be used if desired. Obviously, the data storage associated with the receiver must be sufficient to store the total number of samples expected at the chosen rate for the period that the moveable device is inspecting the pipe.

In another type of analysis, it is not necessary to calculate the average velocity. It is found that sudden changes in pulse velocity as the moveable device moves through a location where there is thinning or damage of the pipe wall. Therefore, very useful information can be gained by analysing the data to determine the rate of change of velocity with time as the device passes different locations.

The high sampling rate permits the detection of both very small changes in velocity with time, and small variations of the velocity from the average. In the embodiment where both the pulse generator and the receiver are on the moveable device, the distance between them is fixed. Therefore, any variation in the time taken for the pulse to travel from the generator to the receiver is due to the change in the pulse velocity through the fluid. As the pulse is sampled at a very high rate (usually 40000 samples per second or greater), very small changes in velocity can be seen.

Where one of the pulse generator and the receiver is on the moveable device and the other is on the pipeline, any changes in velocity of the moveable device in the pipeline must be taken into consideration and corrected for, if one wishes to use the sampling rate to determine pulse velocity or the rate of change of pulse velocity.

Detailed Description of the Embodiments on the Drawings

FIG. 1 shows an embodiment with an untethered ball-like device used as the inspection device. In FIG. 1, 10 indicates a pipeline having a wall 11 of, for example, ductile iron. The pipeline is buried below ground level 1. The pipeline is filled with water 12 at a pressure of approximately 65 psig flowing in the direction 16 at a speed of approximately 0.3 km/hour. The pipeline is for example 0.3 m in diameter, although the invention is useable with pipelines both smaller and larger in diameter than this, and also with pipelines which are at ambient pressure and only partially filled with liquid. It can also be used with pipeline containing gas, for example a pressurized natural gas pipeline.

Three hydrants, generally indicated as 13, 14 and 15 provide access to the pipeline 11. The upper portions of hydrants 13 and 15 are not shown, but their outer casings have been removed and a temporary valve installed to permit entrance and egress of the moveable device of the invention. This is done in a known manner. Hydrant 14 is in its normal condition. It has an external casing 25, a valve 26 and a valve actuator 27 which is a metal rod extending out of the top of the hydrant. Jagged lines 17 indicate an interruption in the drawing which represents a considerable distance (e.g. about 100 m) between the illustrated portions of the pipeline.

The pipeline is externally pitted at 31 and has been thinned by corrosion at 32. These conditions are unknown to the pipeline operator.

A pulse generator station is shown generally at 100, and is associated with hydrant 13. Station 100 comprises a pulse generator 101 attached to the wall 11 of pipeline 10. Pulse generator 101 is connected by cable 102 to computer 104. The pulse generator generates pulses of a series of four pre-set subpulses in the frequency range 500-900 Hz. For example, the subpulses can be 500 Hz., 800 Hz., 650 Hz. and 900 Hz. Each subpulse is generated for 5 ms, so the total length of the pulse is 20 ms. Computer 104 receives a time signal from a GPS satellite system (not shown) using antenna 105. Computer 104 is programmed to cause a pulse (of the four subpulses mentioned above) to be generated by the pulse generator 101 every 2 seconds. The start time of the pulses is repeatable to within +/−50 microseconds. Computer 104 has associated data storage 103 to record each pulse and the time it was generated.

A second optional pulse generator station 200 is associated with hydrant 14. At this station, pulse generator 201 is not attached to the pipeline wall but merely to the metal actuator rod 27 for the metal valve 26 which controls water outflow at hydrant 15. Computer 204 receives a time signal from a GPS satellite system using antenna 205. Computer 204 is programmed to cause pulse generator 201 to generate a single pulse of 20 ms at 1000 Hz every 2.00 seconds, with each such pulse being generated 1 second after the time at which a pulse is to be generated by pulse generator 101. Thus, pulse generator 101 could be set to generate pulses at 1, 3, 5 etc. seconds after each minute commences, and pulse generator 201 could be set to generate pulses at 2, 4, 6 etc. seconds after the minute commences. Computer 204 also comprises data storage 203 which stores a record of each pulse and the time it was generated.

Generally pulse generator station 200 (and possible similar additional pulse generator stations) are used when the pipeline length to be inspected is more than a few hundred metres or has bends.

In the pipeline, a ball-like inspection device 301 of the type shown in Paulson published application WO2006/081671 A1 is rolling along the bottom of the wall 11, propelled by the water flowing through the pipeline. The device has been introduced into pipeline 10 through hydrant 13 as discussed in Paulson published application WO2006/081671 A1. It contains a receiver 302.

Receiver 302 receives low frequency sound in the 200-1200 Hz. range and records it at data storage 303 in inspection device 301. Suitably the data storage 303 is a removable SD memory card. Inspection device 301 also contains a distance measuring device 304 which records the distance travelled by inspection device 301 along the pipeline and records in real time the distance travelled in data storage 303. Suitably, the distance measuring device is a set of three accelerometers arranged orthogonally as disclosed in Paulson published application WO2006/081671 A1, which counts the number of revolutions of the ball-like inspection device as it rolls along the bottom of the pipeline. The inspection device also contains a clock 305 which continuously records a time trace in the data storage 303 and a power supply 306 to power elements 302, 303, 304 and 305. Inspection device 301 rolls along the bottom of the pipeline until it reaches a predetermined location where it is to be retrieved. In FIG. 1, this is hydrant 15. A retrieval device, schematically shown as 20, is ready to retrieve the inspection device. Suitable retrieval devices are described in Paulson published application WO2006/081671 A1.

Once the inspection device 301 has been retrieved from the pipeline, the data in data storage 303 is extracted from it and the average velocity of the sound is calculated for each of the locations at which a pulse was received by receiver 302. It is convenient to display the data on a graph, for easy explanation.

Figure 2:
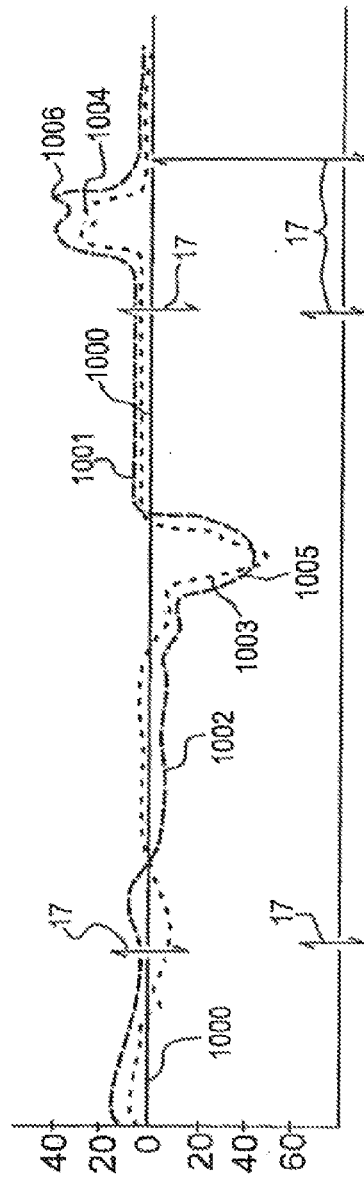
FIG. 2 depicts a graph derived from data gathered by the inspection device of FIG. 1.

Such a graph is shown in FIG. 2. In the graph, average velocity of sound in the water 12 of the pipeline of FIG. 1 is shown by line 1000, which is set as the abscissa (horizontal base line) of the graph. In a typical water pipeline, this average figure is about 1350 metres/second for a pipeline made of ductile iron, and about 675 metres/second in a pipeline made of plastic. The vertical distance above or below this line represents variations from the average velocity of sound in the pipeline, as percentages of the average. The horizontal distance along the graph represents distance that the device has travelled from the hydrant 13. Line 1001 represents the plot of the observed velocity of sound from pulse generator 101 and line 1002 represents the observed velocity of sound from pulse generator 201, expressed as percentages of the average velocity, for the various locations where the receiver has received pulses. For convenience, the horizontal scale corresponds to the distances in FIG. 1. This graph is prepared using the data extracted from data storage 303 after the inspection device has traversed the full distance between hydrants 13 and 15, has been retrieved at hydrant 15 and has had its data extracted.

At most locations, the lines 1001 and 1002 are very close to the average. However, at locations near 31 and 32, there are considerable deviations (here called "excursions") from the average, in the order of more than 10% of the average. For example, the observed velocity of sound as plotted on line 1001 deviates from the average at 1003 by slowing and at 1004 by speeding up. Similarly, the observed velocity of sound as plotted on line 1002 deviates from the average at 1005 by slowing and at 1006 by speeding up.

The locations where the moveable device is located when the observed velocity is significantly lower or higher than the average, as at 1003, 1004, 1005 and 1006 indicate parts of the pipeline where impairment is probable. Further testing or excavation should be carried out at these locations. When FIG. 2 is compared with FIG. 1, it is found that the excursions 1003 and 1005 are associated with the thinning at 32 in FIG. 1, and the excursions at 1004 and 1006 are associated with the pitted region at 31.

It is not necessary to calculate the average velocity, or to display results as shown on FIG. 2 as deviations from the average velocity. Instead, one can calculate for each location the rate of change of velocity from the velocity at the closest previous location for which a measurement is available (typically 0.5-1 m away). A table or plot of the rate of change of velocity against locations also shows the same excursions, and may be preferred as a means of displaying the data.

Figure 3:
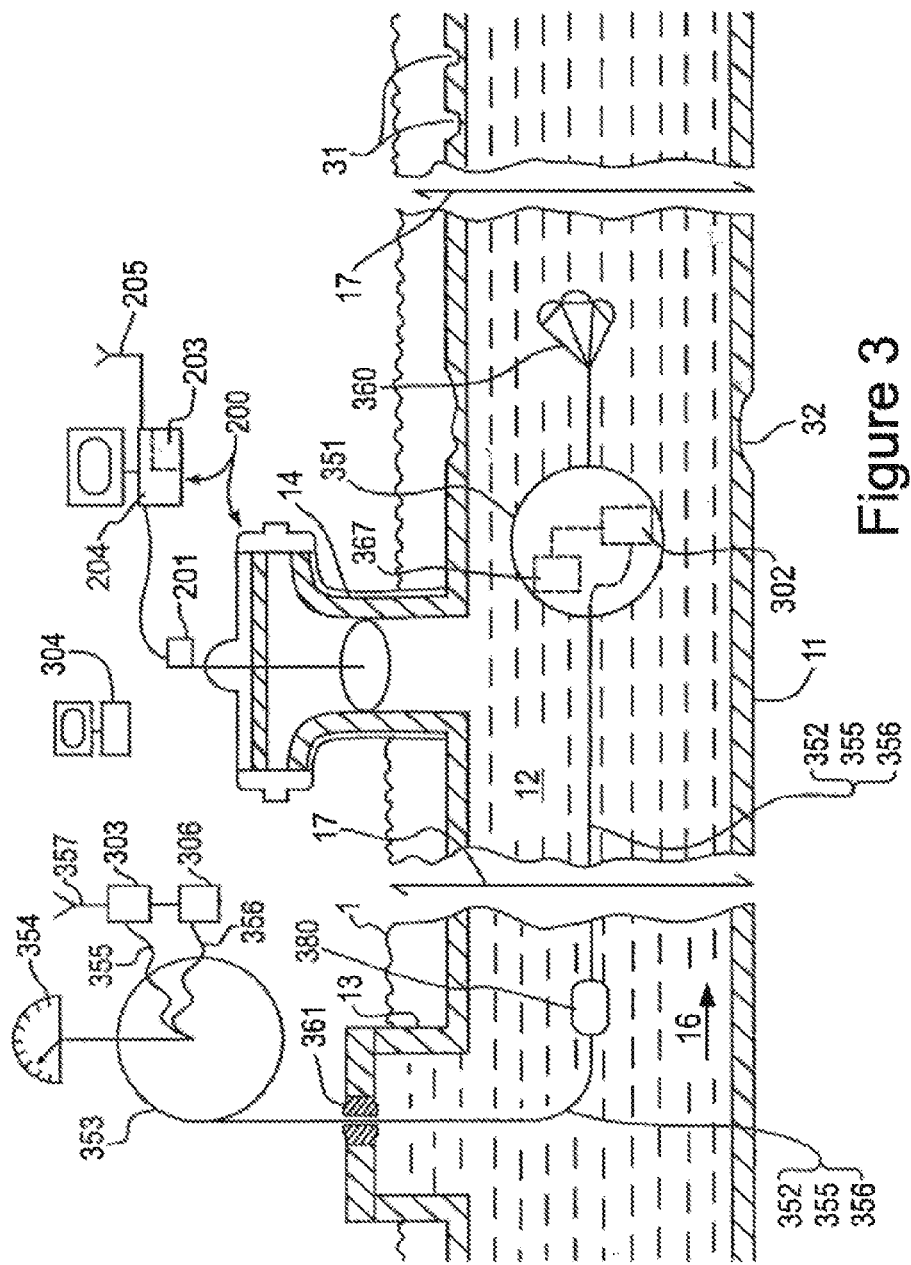
FIG. 3 is a cutaway view, not to scale, of a station and a pipeline in which a tethered moveable inspection device of the invention is moved with or against liquid flow by adjusting the length of its tether.

FIG. 3 depicts a further embodiment. In FIG. 3, the same numerals as in FIG. 1 are used where like elements are shown. These elements will not be described further.

In FIG. 3, the moveable inspection device is a tethered inspection device 351 attached to a tether 352. It is deployed by a parachute 360 which causes it to move in the direction 16 of fluid flow, to the limit of the tether 352. The tether 352 passes through a suitable liquid-tight fitting 361 which is temporarily attached to hydrant 13, then out of hydrant 13 to a drum 353. The position of the inspection device 351 is controlled by winding or unwinding the tether, and the location of the inspection device 351 is determined by noting the number or revolutions of the drum 353 (as by reading gauge 354, which can be done electronically, with the result being stored in data storage 303), calculating from this the number of metres of cable paid out and subtracting the cable extending from the drum to the pipeline. In the configuration shown, the tether contains a suitable cable 355 to connect the receiver to the data storage 303, which is located outside the pipeline. Also, no clock is present. Instead, there is an antenna 357 and associated electronics to obtain a GPS time signal and to record it continuously in the data storage 303. The embodiment shown has a data storage 303 which can be removed and taken to a remote computer 304 for processing of the collected data. Alternately, if desired, the computer can be directly connected to the data storage, or the data storage can be part of the computer as shown in the embodiment of FIG. 1.

In the embodiment illustrated, power supply 306 is located outside the pipeline. Power for the receiver 302 is supplied for example by a cable 356 passing through the tether from the power supply 306 to the receiver 302. In many situations, however, it may be simpler and cheaper to provide a separate power supply for the receiver, being a battery 367 in the mobile inspection device.

In the embodiment of FIG. 3, only one pulse generator station on the pipeline is shown, at 200 on hydrant 14, but more than one can be used if desired. For example, a pulse generator station could be placed on hydrant 13, or attached to the pipeline at any other place where the pipeline is easily accessible.

A pulse generator can also be placed on the tether, as shown at 380, spaced a known distance from the receiver 302. Alternately, a second receiver can be placed at 380. If a pulse generator is placed at 380, it functions similarly to pulse generator station 100 in FIG. 1. If, instead, a receiver is placed at 380, it functions similarly to receiver 302, and its data can conveniently be collected in data storage 303.

The data stored in data storage 303 is treated in the same manner as the data collected in the embodiment of FIG. 1. If 380 is a receiver, data from receiver 380 is also stored in data storage 303, and is used in an analogous manner to data from receiver 302. If 380 is a station, the times of its pulses are stored in data storage 303.

Figure 4:
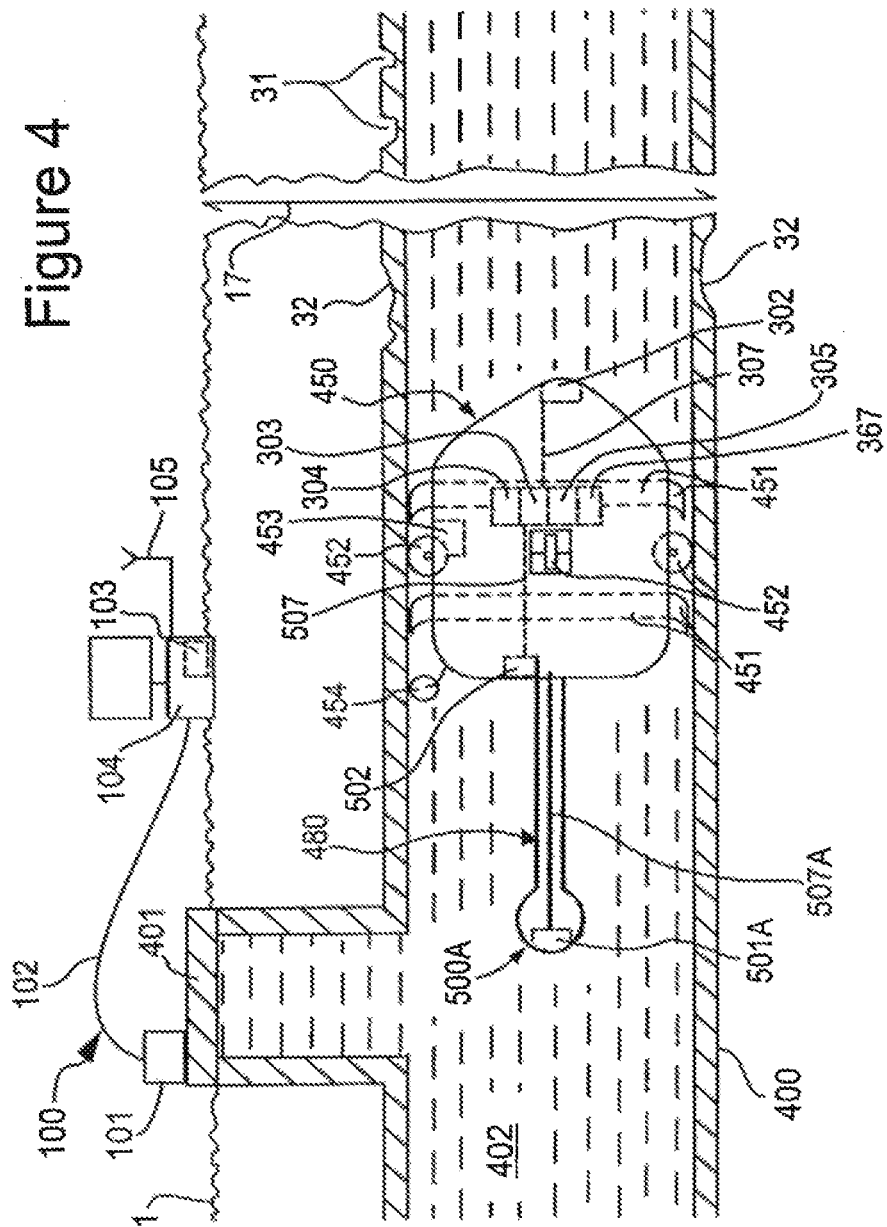
FIG. 4 is a cutaway view, not to scale, of a pipeline in which a pipeline pig equipped according to the invention moves in the pipeline, propelled either by fluid flow or a motor.

FIG. 4 depicts a further embodiment. In FIG. 4, the same numerals as in FIG. 1 are used where like elements are shown. These elements will not be described further.

In FIG. 4, the pipeline 400 is an oil pipeline, which has no hydrants. It is filled with oil 402. The pipeline has pigging stations (not shown) for entry and exit of pipeline pigs. It also has inspection ports, one of which is shown at 401. The pulse generator station 100 described in FIG. 1 is arrayed at inspection port 401, with the pulse generator 101 attached to the outside of the inspection port.

The moveable inspection device is a pipeline pig 450, which has conventional seals 451 which contact or nearly contact the wall 11 of the pipeline so that the pig is pushed along by the flow of the oil. The pig contains receiver 302, data storage 303, clock 305, battery 367 and suitable cabling 307 for them. Storage 303, and clock 305 function as in the embodiment of FIG. 1, except the data on distance travelled which is received by data storage 303 comes from a distance measuring device such as odometer 454 and the power to operate them comes from battery 367. The pig preferably employs wheels 452 to assist in moving the pig through the pipe as quietly as possible. Optionally, these wheels can be powered, so that the pig can move independently of the fluid flow. A motor 453 is shown in dashed form to provide power to the wheels. The motor can conveniently be powered by battery 367. The necessary cabling connections are not shown, to simplify the drawing. If the pig is powered, it does not need seals 451.

If desired, the pig can carry a pulse generator station 500. This comprises pulse generator 501 which emits pulses at intervals timed by the clock 305 and which is powered by power source 306, which has to have sufficient power to supply this as well as the other components. Cabling 507 connects the pulse generator with the clock 305, data storage 303 and power source 306. The pulse generator 501 should be spaced at least one pipe diameter from receiver 302, and preferably as far distant from the receiver 302 as possible having regard to the constraints in pig length imposed by the size of the pigging stations on the pipeline.

The pulse generator 501 emits pulses as described with respect to pulse generator 201 in FIG. 1, at a different frequency from those of pulse generator 101 so that the pulses from pulse generators 101 and 501 can be distinguished from one another. The pulses are recorded in the data storage 303 just as the pulses from pulse generators 101 and 201 are recorded in the embodiment of FIG. 1. The time trace from clock 305 is also stored in data storage 303. The data stored in data storage 303 is treated in the same manner as the data collected in the embodiment of FIG. 1.

If desired, pulse generator station 100 and pulse generator 101 can be omitted, and pulse generator 501 can be the only pulse generator present.

In a further alternative embodiment, useable when the pigging station architecture permits it, the pig 450 has a boom 480, on which is mounted pulse generator station 500A with a pulse generator 501A. Boom 480 carries cabling 507A, which connects the pulse generator with the clock 305, data storage 303 and power source 306. When pulse generator station 500A and its associated pulse generator 501A are present, station 500 and pulse generator 501 are omitted, as shown in FIG. 4A. Boom 480, station 500A, pulse generator 501A and cabling 407A are an optional variation. The extra length of the boom permits the pulse generator 501A to be at a longer distance from receiver 302 than is possible with pulse generator 501.

If receiver 302 and either pulse generator 501 or 501A are present, the data storage 303 can if desired be associated with a computer 304 which directly processes the data received. The velocity of the pulses passing between station 501 or 501A and receiver 302 is easy to calculate, as the distance between them is fixed, and the only data necessary to determine velocity is the time taken for the pulse to pass from the pulse generator to the receiver.

In a further alternative embodiment of FIGS. 4 and 4A, there is no pulse generator 501 or 501A or boom 480, but instead there is a second receiver 502 on the pig. Receiver 502 receives pulses from pulse generator 101, and sends data as to the pulses that it receives to form a trace in data storage 303 through cabling 507. The distance between receivers 302 and 502 is known, as both are in fixed positions on the same pig. Analysis of the data trace from receiver 502 gives a check on the data collected at receiver 302, thus leading to increased certainty in the locations where wall impairment has been found.

Figure 5:
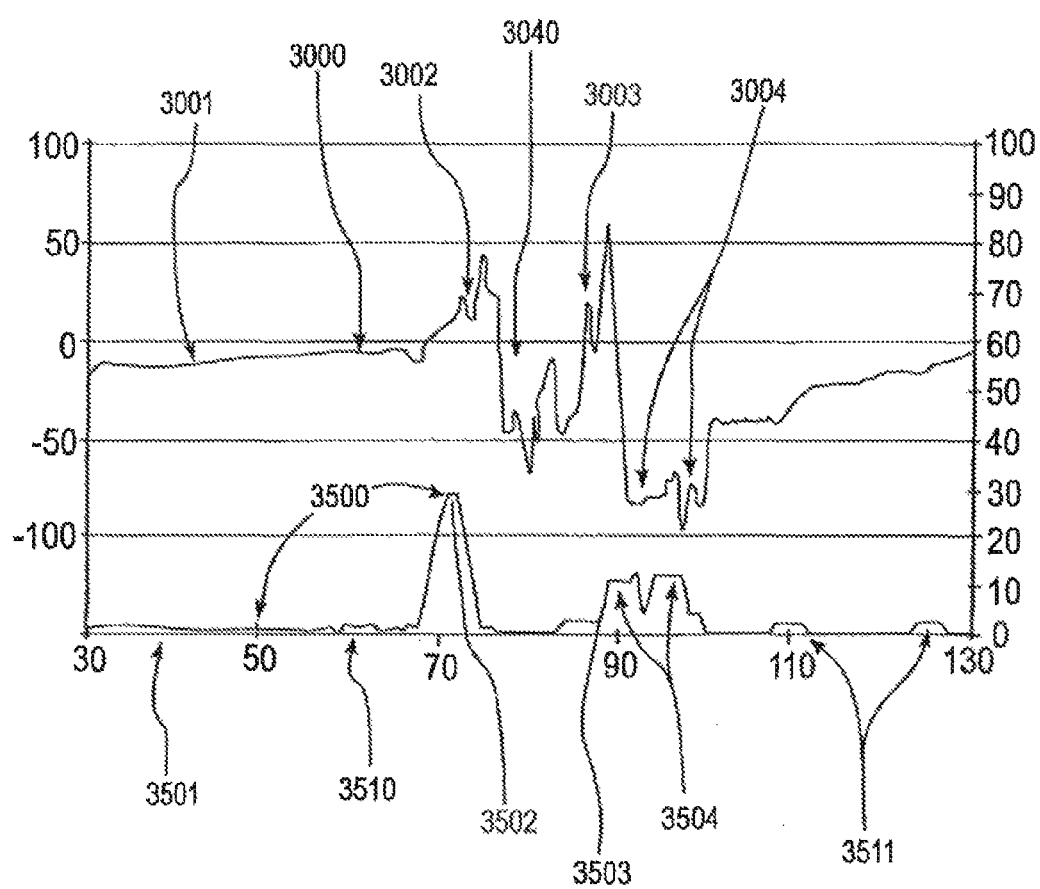
FIG. 5 is a graph showing results from an actual pipe inspection using one embodiment of the inventive device.

FIG. 5 presents results from Example 3, and will be described below in the context of that Example.

EXAMPLES

Example 1

Pipe lengths were obtained for the purpose of preparing a test pipeline. These included two new, undamaged 20 ft (6.09 m) lengths of ductile iron pipe having an internal diameter of 300 mm. and a nominal wall thickness of 0.45 inch (1143 mm), two 20 foot (6.09 m) sections of 300 mm internal diameter ductile iron pipe which had been retrieved from a pipe replacement operation in a municipal water system, and a 20 foot (6.09 m) PVC pipe of 300 mm interior diameter and a nominal wall thickness of 0.406 inch (10.31 mm).

The two damaged pipe lengths were examined visually and ultrasonically. Their original nominal wall thickness was not known. They were found to be pitted and corroded in places. A grid was drawn on each pipe length and all the damages were photographed and quantified by measuring the areas and the depth of each visually-perceivable damaged area.

A test pipeline was assembled from the pipe lengths described above. The order of assembly was the two new pipe lengths, one of the damaged lengths, the plastic length and then the second damaged length. At each end of the test pipeline, a 90 degree ductile iron elbow was placed, turned so that the open end faced upwards. Adjacent lengths were joined with suitable watertight connections. This permitted water to be retained in the test pipeline, when the pipeline was approximately horizontal.

The test pipeline was mounted on a wooden test stand. The part between the two elbows was approximately horizontal, with variations as noted below. The pipe was filled with tap water from the municipal water system of Calgary, Alberta, to a level part way up the elbows. A pulse generator built by Pure Technologies Ltd. was attached to the outside of one of the elbows by being strapped in place. This pulse generator generated a 2 ms pulse of acoustic energy at 400 Hz, repeated every 2.0 seconds for ten repeats when the operator actuated it. The pulse generator was connected to a computer (which served as a data storage and which also stored a GPS time signal. Thus, the precise time each pulse was sent could be ascertained by examining the data stored on the computer.

A hydrophone, Model: VHLF (manufactured by VEMCO Division AMIRIX System Inc.) was placed on an aluminum wheeled cart moveable along the bottom of the pipe. The cart was mechanically decoupled from the hydrophone. The hydrophone was connected by suitable cables to the computer so that data from the hydrophone was also stored on the computer. The computer sampled the hydrophone output 96000 times a second. It was thus possible by examining the data from the pulse generator, the hydrophone and the GPS signal in the computer data storage to determine exactly when a pulse was sent by the pulse generator and when it was received at the hydrophone.

The cart with the hydrophone was pulled through the generally horizontal test pipe by a string. Its position in the pipe was determined by noting the length of string pulled from the pipe. This permitted the distance from the pulse generator to the hydrophone to be calculated.

Pulses were sent from the pulse generator to the hydrophone with the hydrophone at various known distances from the pulse generator. Ten pulses were sent with the hydrophone in each position. The time of sending and the time of each pulse were recorded. From this information, the travel time of each pulse was calculated. For each location, data from 10 pulses was recorded and the travel time averaged. For almost all locations, variation in travel time did not exceed +/−25 microseconds. From the averaged travel time and the distance between the location and the pulse generator, the velocity of travel when the hydrophone was at that location was determined.

The velocities calculated for all locations during each test run were averaged to give an average velocity of sound in the test pipeline.

When the five pipe sections were horizontal, air pockets occurred at some of the sections. The presence of air pockets was verified by a submerged camera. Test runs were done with such air pockets present, and further test runs were done with the pipe tilted to an angle of 2-3 degrees from horizontal, which permitted the air to escape so that the pipe was fully water filled.

Initially, anomalous results were obtained which indicated sound velocities which were different from the average when the hydrophone was at several locations in the new ductile iron pipe lengths. This was unexpected, so the apparatus was disassembled and the two new iron pipe lengths were examined ultrasonically. It was found that they departed from the nominal wall thickness in the places where the results were different from the average. In one location, the new iron pipe had a wall thickness of 0.361 inch (9.17 mm) and, in another, it had a wall thickness of 0.558 inch (14.17 mm). Therefore, a grid was prepared showing wall thickness of the undamaged pipe lengths, just as had been done for the damaged lengths.

It was found that the velocity of the pulses between the pulse generator and the hydrophone when the pulse generator was attached to the pipe reliably predicted whether the pipe was or was not damaged or different from the average thickness at the location where the hydrophone was when the signal was received.

It was also found that the presence of air pockets caused a large change in velocity. This was expected, as the speed of sound depends on the medium through which the sound travels. In the test set-up, the result could have been misread as a change in velocity due to a variation in wall thickness, had it not been known that air pockets were present because of the images from the submerged camera. In a field operation where the water is flowing, change in velocity from air pockets can easily be distinguished because of the characteristic noise associated with an air pocket.

When the hydrophone was in the plastic pipe, the velocity dropped to an average velocity over the pipe length of approximately 500 m/s as compared to an average velocity in the undamaged metal pipe of approximately 1300 m/s. Further, when the hydrophone was located in a metal pipe, with the plastic pipe in the pipe string between it and the pulse generator, the recorded velocity was lower than would otherwise have been expected. This shows that the method of the invention can locate pipe lengths of a different material than the remainder of the pipeline. Such information can be of practical importance in actual pipelines, as it can show that an undocumented replacement of a pipe section has occurred.

Example 2

In a further series of test runs, the pulse generator was removed from the elbow and was instead placed on the cart, at a spacing of 1.00 m from the hydrophone, and was connected to the computer by suitable cables. This fixed the known distance between the hydrophone and the pulse generator at 1.00 m., irrespective of the location of the hydrophone within the test pipeline.

The test runs with the hydrophone and pulse generator both mounted on the wheeled cart gave similar results to those where the pulse generator was strapped to the elbow.

Example 3

Access for test purposes was obtained to a municipal water delivery pipeline in the City of Calgary, Canada. The pipeline was one which was to be removed and replaced as part of the municipality's normal infrastructure upgrading. It was a 30 year old 300 mm internal diameter poly-bagged ductile iron pipeline. The condition of the pipe was unknown. The pipeline was still water-filled and connected to normal municipal water supplies at the normal municipal water pressure of 60 psig. (4.137 bar).

A pulse generator designed to emit pulses 20 ms long every 3 seconds at a frequency of 500 Hz. was attached to a valve actuator which connected to the pipeline. The pulse generator was connected with a GPS time signal and a data storage to form a station according to the invention.

A ball detector unit of the type described in Paulson published application WO2006/081671 A was equipped with an accelerometer capable of receiving the frequency emitted by the pulse generator, a data storage and a precise clock which had been synchronized with a GPS time signal. The accelerometer sampled for a pulse 40000 times per second, and stored the samples in an on-board data storage.

Flow was induced in the pipeline by opening another hydrant beyond the length of pipeline being tested.

The ball detector unit was inserted into the pipeline through a hydrant and was moved by the water flow in the pipeline to the opened hydrant 356 m away where it was retrieved by flushing the ball out of the pipe using the flow out of the opened hydrant. The travel of the ball between the two hydrants included passage through 100 m of line which was to be excavated and removed as part of the infrastructure upgrade. The pulse generator was attached 30 m before the beginning of this 100 m length of the pipeline. Pulses were sent by the pulse generator and received by the accelerometer on the ball detector unit. The location of the ball at the time each pulse was received was determined by counting ball rotations as discussed in Paulson published application WO2006/081671A. The accelerometer data and the time data from the clock in the ball were stored as separate traces in the same data storage as the data for calculating ball location. The ball moved through the pipeline at a speed of approximately 0.5 m/sec, resulting in one pulse being received for approximately every 1.5 metre of travel. After the ball was retrieved, the velocity of sound travelling from the pulse generator to the ball location was calculated for each location at which the ball had received a pulse. The average velocity over the entire 356 m length was also calculated.

The results are shown by the line 3000 in FIG. 5, which shows the percentage difference at each location of the velocity measured at that location from the average velocity. The horizontal scale is the distance from the pulse generator in metres, and the left hand scale shows the deviation from the average as a percentage.

In calculating the deviation from the average, it was assumed that the velocity of the ball remained constant, and that all variation in the time taken for the pulse to travel from the pulse generator to the receiver arose from a change in the apparent velocity of sound.

Subsequently, the 100 metres of pipeline were disconnected from the municipal water system, excavated, and replaced with a new pipeline, as part of the municipality's infrastructure upgrade. As each pipe length was excavated, it was photographed and examined. All external damage was noted, and was expressed as cm$^2$ of damaged surface per metre of pipe length.

The data is placed on FIG. 5 as line 3050, using the same horizontal scale as used for line 3000. The vertical scale is on the right, and shows cm$^2$ of damaged surface per metre of pipe length at that location.

It will be noted that where the line 3500 shows no apparent damage, the line 3000 is very close to the average velocity of sound over the whole test. See for example position 3001 on line 3000 and position 3501 on line 3050. Positive excursion 3002 on line 3000 corresponds closely to damage noted at 3502. Negative excursion 3003 corresponds almost exactly with damage 3503. Similarly, negative excursion 3004 (which goes off scale at the bottom of the graph) corresponds with damage 3504.

There is a positive excursion at 3030 which corresponds with the beginning of the damage 3504, but which quickly changes to negative excursion 3004. It is not known why some excursions are positive and some are negative.

Very small amounts of visible damage, as at 3510 and 3511, do not correspond with any excursion.

There is an excursion at 3040 which does not correspond to observed damage. However, any damage or corrosion on the inside of the pipe was not catalogued, and this excursion may correspond to damage or weakening of the pipe that was not visible from the outside.

The results of this test demonstrate that excursions, either positive or negative, from the average velocity of sound tend to indicate that, at the time the excursion occurs, the moveable inspection device is passing through a location in the pipeline where the pipe has damage.

It is understood that the invention has been described with respect to specific embodiments, and that other embodiments will be evident to one skilled in the art. The full scope of the invention is therefore not to be limited by the particular embodiments, but the appended claims are to be construed to give the invention the full protection to which it is entitled.

What is claimed is:

1. A method for determining locations of impairment in the wall of a pipeline which contains a fluid, comprising:
    moving a moveable device through the pipeline in contact with the fluid,
    generating a series of acoustic or seismic pulses at a pulse generator receiving the acoustic or seismic pulses at a receiver,
    at least one of said pulse generator and receiver being on the moveable device, and
    determining, when the device is at each of a plurality of locations along the pipeline, either the velocity of travel of such pulses between the pulse generator and the receiver or the rate of change of such velocity as the device passes each such location,
    said pulses having at least one of
        (i) a frequency of from 20 Hz to 2000 Hz or
        (ii) a wavelength of from 1.5 to 75 times the diameter of the pipeline in which the method is performed.

2. A method as claimed in claim 1, in which said seismic or acoustic pulses are generated at a pulse generator at a fixed location with respect to the pipeline wall, and are received at a receiver on the moveable device.

3. A method as claimed in claim 1, in which said seismic or acoustic pulses are generated by a pulse generator mounted on said moveable device, and received at a receiver mounted on said moveable device.

4. A method as claimed in claim 3, in which the pulse generator is separated from the receiver by a distance of at least one diameter of the pipeline.

5. A method as claimed in claim 1 in which the pulses are at a frequency of from 20 Hz to 500 Hz.

6. A method as claimed in claim 1 in which the pulses have a wavelength of from 5 to 15 times the diameter of the pipeline in which the method is performed.

7. A method as claimed in claim 1 in which the fluid is water.

8. A method as claimed in claim 1 in which the fluid is oil.

9. A method as claimed in claim 1 in which the moveable device is tethered and is moved within the pipeline by reducing or increasing the length of its tether.

10. A method as claimed in claim 1 in which the moveable device is a pipeline pig.

11. A method as claimed in claim 1, in which the moveable device is an untethered ball which rolls along the bottom of the pipeline.

12. A method for determining locations of impairment in the wall of a pipeline which contains a liquid, comprising:
    providing a pipeline pig which has a pulse generator to generate pulses, and, spaced from said pulse generator, a receiver for said pulses,
    moving said pig through the pipeline in contact with the liquid,
    generating acoustic or seismic pulses having frequencies in the 20 Hz to 2000 Hz range with said pulse generator as said pig moves through the pipeline, and
    receiving the acoustic or seismic pulses at the receiver.

13. A method as claimed in claim 12, comprising the step of determining the velocity of the pulses travelling from said pulse generator to said receiver when the pig is in each of a plurality of locations within said pipeline.

14. A method as claimed in claim 12, comprising the step of determining the rate of change of velocity of the pulses travelling from said pulse generator to said receiver when the pig is moving past each of a plurality of locations within said pipeline.

15. Apparatus for determining locations of impairment in the wall of a pipeline, which comprises
    a pipeline pig moveable through the pipeline
    an acoustic or seismic pulse generator which generates pulses at a frequency in the range of 20 Hz. to 2000 Hz.
    a receiver for acoustic or seismic pulses generated by said generator
    both of said pulse generator and said receiver being located on the pipeline pig at a fixed distance from one another, and
    means for determining the location of the pipeline pig in a pipeline.

16. Apparatus for determining locations of impairment in the wall of a pipeline which contains a fluid, which comprises
    a moveable device moveable through the pipeline in contact with the fluid
    an acoustic or seismic pulse generator for generating pulses in said fluid at a frequency of from 20 Hz to 2000 Hz
    a receiver for acoustic or seismic pulses generated by said generator
    one of said pulse generator and said receiver being located on the moveable device
    time measuring means to record when pulses are emitted by the pulse generator and when pulses are received by the receiver, and
    means for determining the location of the moveable device in a pipeline.

17. Apparatus for determining locations of impairment in the wall of a pipeline which contains a fluid, which comprises
    a moveable device moveable through the pipeline in contact with the fluid
    an acoustic or seismic pulse generator for generating pulses in said fluid at a frequency of from 20 Hz to 2000 Hz
    a receiver for acoustic or seismic pulses generated by said generator
    one of said pulse generator and said receiver being located on the moveable device
    means for determining either (a) the velocity of pulses travelling between the pulse generator and the receiver or (b) the rate of change of velocity of pulses travelling between the pulse generator and the receiver, and
    means for determining the location of the moveable device in a pipeline.

* * * * *